United States Patent [19]

Trumbull et al.

[11] Patent Number: 5,263,629

[45] Date of Patent: Nov. 23, 1993

[54] METHOD AND APPARATUS FOR ACHIEVING HEMOSTASIS ALONG A STAPLE LINE

[75] Inventors: Horace R. Trumbull, Sharonville, Ohio; Mary E. Kay, Charlotte, N.C.; Bernard J. Durman, Loveland, Ohio; Brenton K. Ahrens, West Chester, Ohio; James H. Chambers, Milford, Ohio

[73] Assignee: Ethicon, Inc., Cincinnati, Ohio

[21] Appl. No.: 905,808

[22] Filed: Jun. 29, 1992

[51] Int. Cl.$^5$ .............................. A61B 17/00
[52] U.S. Cl. .................... 227/181; 227/19; 227/175; 227/176; 227/180; 606/151; 128/898
[58] Field of Search ............... 227/176, 180, 181, 19; 128/898; 600/37; 602/53, 79, 900; 604/374; 606/151, 213, 215, 219, 220

[56] References Cited

U.S. PATENT DOCUMENTS

| | | | |
|---|---|---|---|
| 2,758,112 | 8/1956 | Waning | 604/374 |
| 3,079,606 | 3/1963 | Bobrov et al. | |
| 3,122,140 | 2/1964 | Crowe | 604/374 |
| 3,490,675 | 1/1970 | Green et al. | |
| 4,397,311 | 8/1983 | Kanshin et al. | 227/180 |
| 4,520,817 | 6/1985 | Green | |
| 4,548,202 | 10/1985 | Duncan | 606/220 |
| 4,626,253 | 12/1986 | Broadnax, Jr. | 604/374 |
| 4,633,861 | 1/1987 | Chow et al. | |
| 4,633,874 | 1/1987 | Chow et al. | |
| 4,731,277 | 3/1988 | Groitzsch et al. | 604/374 |
| 4,784,137 | 11/1988 | Kulik et al. | |
| 4,840,626 | 6/1989 | Linsky et al. | 604/364 |
| 4,892,244 | 1/1990 | Fox et al. | |
| 4,930,674 | 6/1990 | Barak | 227/179 |
| 4,955,959 | 9/1990 | Tompkins et al. | |
| 5,042,707 | 8/1991 | Taheri | 606/213 |
| 5,104,025 | 4/1992 | Main et al. | |
| 5,123,528 | 6/1992 | Brown et al. | 53/432 |
| 5,134,229 | 7/1992 | Saferstein et al. | 606/213 |

FOREIGN PATENT DOCUMENTS

1156529 11/1983 Canada ................ 606/213

OTHER PUBLICATIONS

Johnson & Johnson brochure entitled, "Surgicel and Surgicel Nu-Knit Absorbable Hemostat," Jun. 1989 (2 sheets).
John & Johnson brochure entitled, "Interceed (TC7) Absorbable Adhesion Barrier," Sep. 1989 (1 sheet).
Johnson & Johnson brochure entitled, "Instat Collagen Absorbable Hemostat" Sep. 1985 (1 sheet).
Ethicon product brochure entitled, "Proximate Surgical Staplers—Design and Operation," Undated (5 sheets).

Primary Examiner—Stephen C. Pellegrino
Assistant Examiner—J. A. Schmidt
Attorney, Agent, or Firm—Dressler, Goldsmith, Shore & Milnamow, Ltd.

[57] ABSTRACT

A method and apparatus to achieve hemostasis along a staple line by utilizing a pledget material positioned adjacent at least one surface of tissue. A line of staples extends through the tissue and the pledget material. The pledget material substantially uniformly distributes pressure along the staple line and thereby causes substantial hemostasis along the tissue cut. The pledget material may also absorb blood that may escape from a partially open blood vessel.

15 Claims, 3 Drawing Sheets

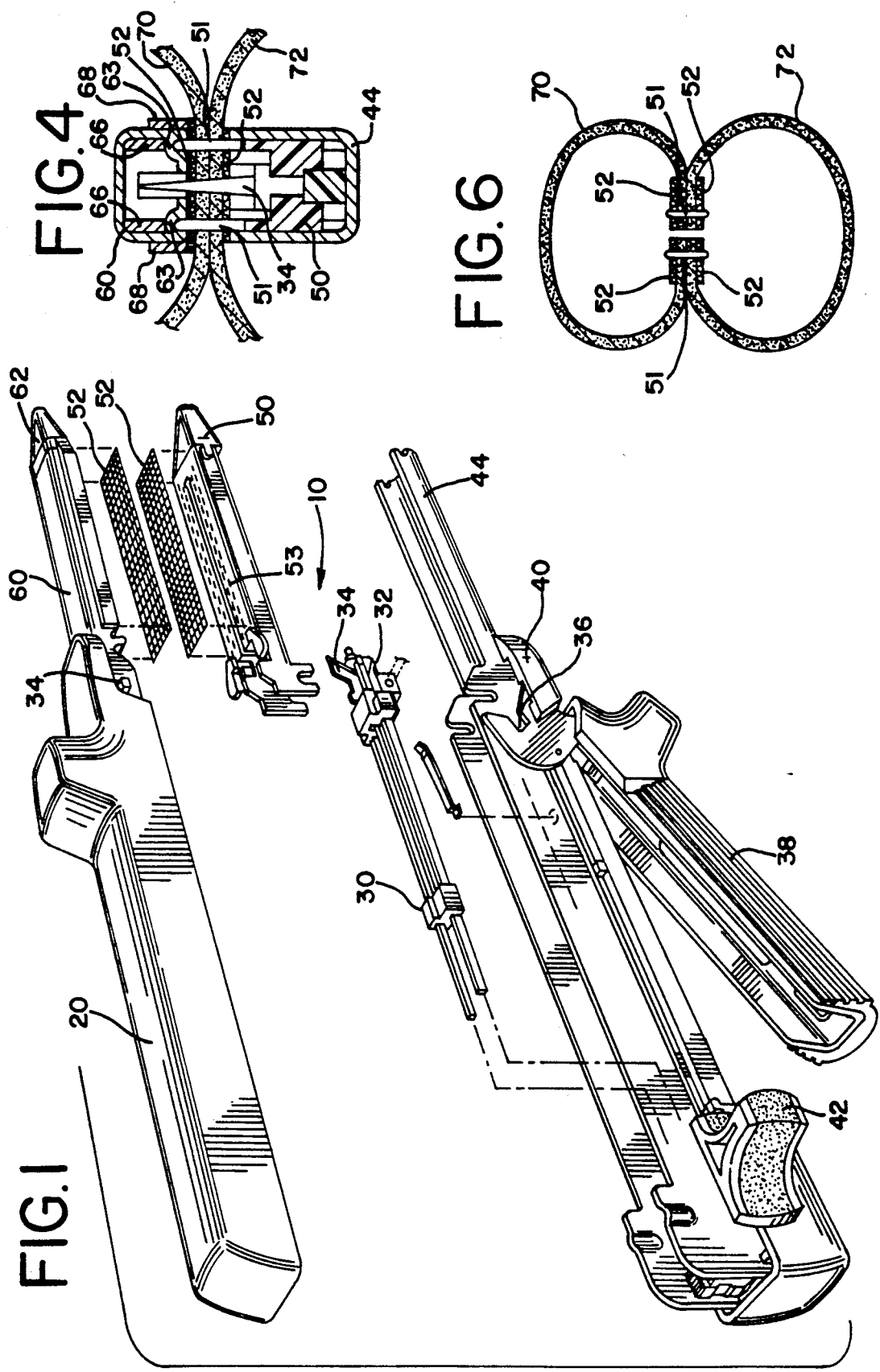

METHOD AND APPARATUS FOR ACHIEVING HEMOSTASIS ALONG A STAPLE LINE

FIELD OF THE INVENTION

The present invention is generally directed to a method and an apparatus for achieving hemostasis along a tissue cut having open blood vessels that utilizes a line of surgical staples. More specifically, the invention relates to a method and an apparatus for achieving hemostasis during the resection and anastomoses of the walls of two adjacent body organ sections by utilizing a pair of spaced apart parallel lines of surgical staples.

BACKGROUND OF THE INVENTION

During certain surgical procedures it is necessary to cut organ tissue and apply one or more rows of surgical staples along the tissue cut to close the open blood vessels. Surgeons have used linear cutter stapling devices to suture body organs and tissues such as lung, esophagus, stomach, duodenum and other body organs in the intestinal tract. Such devices apply a plurality of laterally spaced rows of staples on opposite sides of a tissue cut.

Example of such surgical staplers are disclosed in U.S. Pat. Nos. 4,633,861 and 4,892,244, the disclosures of which are incorporated herein by this reference. The surgical stapler includes a pair of cooperating elongate jaw members. One of the jaw members includes a staple cartridge with at least two laterally spaced rows of staples and the other jaw member includes an anvil with staple closing depressions in alignment with the rows of staples in the cartridge. A pusher block is directed longitudinally along the jaws to sequentially eject staples from the cartridges in a manner that closes the staples against the anvil to form laterally spaced lines of staples through tissue that is gripped between the jaws. A knife is associated with the pusher block so as to move forward along the jaws to cut the tissue along the line between the previously formed staple rows.

It is necessary to close all of the open blood vessels along the cut line between the staple rows formed by a linear cutter or similar type surgical device. Prior efforts have been directed to modifying the staple design and staple pattern to increase the level of hemostasis along the cut line. The present invention is specifically directed to a unique method and apparatus for achieving a higher level of hemostasis than has heretofore been possible with existing stapling techniques and stapling devices.

SUMMARY OF THE INVENTION

The present invention provides a method and apparatus to achieve hemostasis along a staple line by utilizing a pledget material positioned adjacent at least one surface of the tissue. The line of staples is formed so as to extend through the tissue and the absorbable pledget material. The pledget material is selected so as to substantially uniformly distribute pressure along the staple line and thereby cause substantial hemostasis along the tissue cut. The pledget material is also preferably selected to absorb any blood that may escape from a partially open blood vessel.

It has been determined that hemostasis is further enhanced by providing a pledget material adjacent both surfaces of the tissue being joined and extending the staples therethrough.

In accordance with an exemplary application of the invention, a surgical stapling device is provided for cutting and adjoining together the adjacent walls of two organ sections that achieves hemostasis along the staple line. The stapling device includes a means for clamping the adjacent walls of the organ sections together with an absorbable pledget material positioned adjacent the surface of at least one of the organ section walls. A stapling means forms at least one pair of spaced apart parallel lines of surgical staples extending through the walls of the organ sections and the absorbable pledget material so as to substantially uniformly distribute pressure along the lines of the staples. A blade means cuts the walls of the organ sections and the pledget material between the line of surgical staples so in a manner that closes the open blood vessels and cause substantial hemostasis along the cut in the walls of the organ sections. The stapling device preferably positions an absorbable pledget material adjacent each of the outer surfaces of the organ section walls.

It is contemplated that the principles of the present invention may be utilized in conjunction with other types of surgical staplers or cutters such as linear or circular staplers, linear cutters and intraluminal staplers.

BRIEF DESCRIPTION OF THE DRAWINGS

FIG. 1 is an exploded view in perspective of a surgical stapler device incorporating the hemostasis achieving features of the present invention;

FIG. 4 is a sectional view taken through the jaws of the surgical stapler showing a staple being formed through adjacent tissue sections and pledget material positioned adjacent the outer surface of each of the tissue sections;

FIG. 6 is a transverse sectional view showing adjacent organ segments joined together by staples and pledget material in accordance with the invention (shown upside down;

DETAILED DESCRIPTION OF PREFERRED EMBODIMENT

Figure 5:
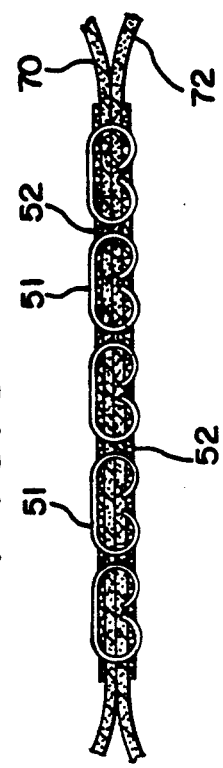
FIG. 5 is a longitudinal sectional view showing adjacent tissue sections joined together by staples and pledget material in accordance with the invention.

Referring to FIG. 1, there is shown a typical surgical stapler 10 generally of the type disclosed in U.S. Pat. Nos. 4,633,861 and 4,892,244, the disclosure of which patents are incorporated herein by reference for a more complete discussion of certain structure details of the device. Surgical stapler 10 includes an upper jaw 20, a firing means 30, a lower jaw 40 and a staple cartridge 50 that is received within the lower jaw 40.

The firing means 30 includes a pusher block and firing wedge assembly 32 and a knife 34 located therebetween. The firing wedges are directed through longitudinal slots located in staple cartridge 50. Cartridge 50 is releasably received within a lower jaw channel 44. A firing knob 42 activates the firing means 30 to move the firing wedges 32 through the staple cartridge 50. As the firing wedges 32 pass longitudinally through the cartridge they contact staple drivers (not shown), which in turn eject the staples through openings 53 in the staple cartridge 50.

Figure 2:
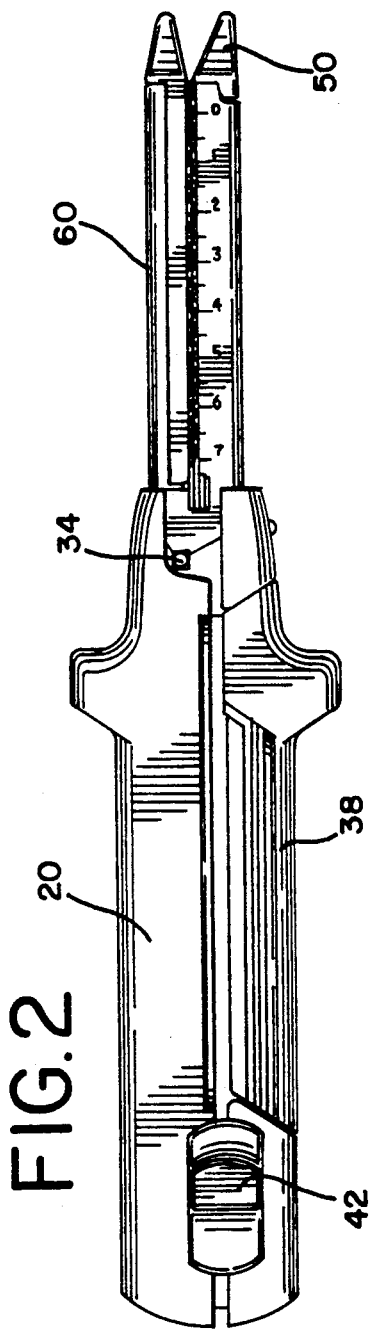
FIG. 2 is a side elevational view of the stapler device shown in FIG. 1 with its jaws in a clamping position.

Upper jaw 20 is pivotally connected to lower jaw 40 through a latch pin 34 that is received in a slot 36 associated with a latch member 38 to latch the jaw members together at an intermediate position along the length thereof. Movement of latch member 38 between its latched position, as shown in FIG. 2, and its unlatched position, as shown in FIG. 1, causes the jaws 20 and 40 to move toward and away from each other.

Figure 3:
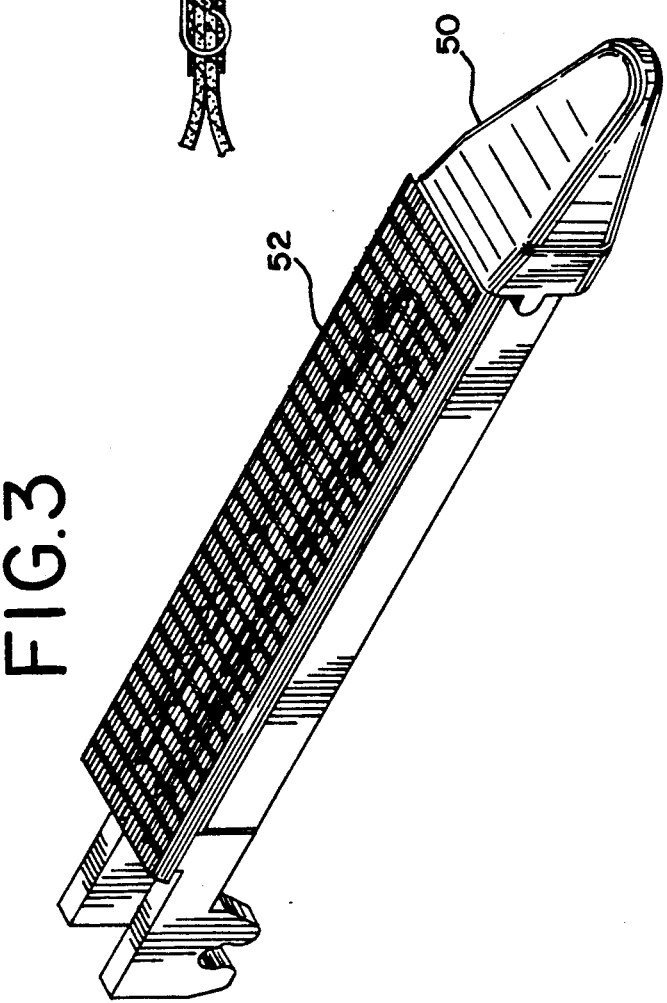
FIG. 3 is a perspective view of a staple cartridge that includes a pledget material in accordance with the invention.
Figure 7:
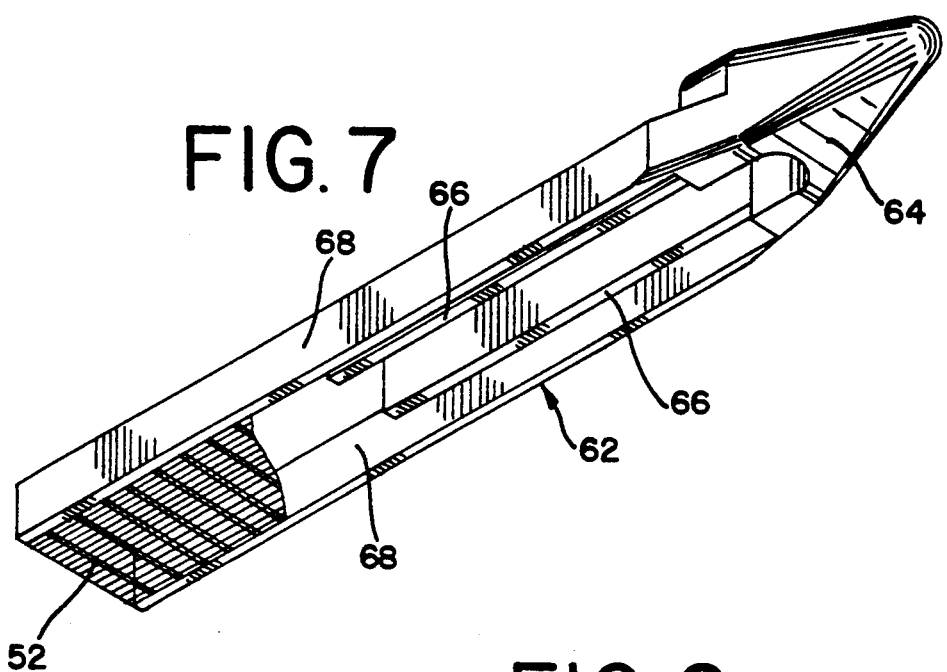
FIG. 7 is a perspective view of an anvil tip that includes a pledget material in accordance with the invention.
Figure 8:
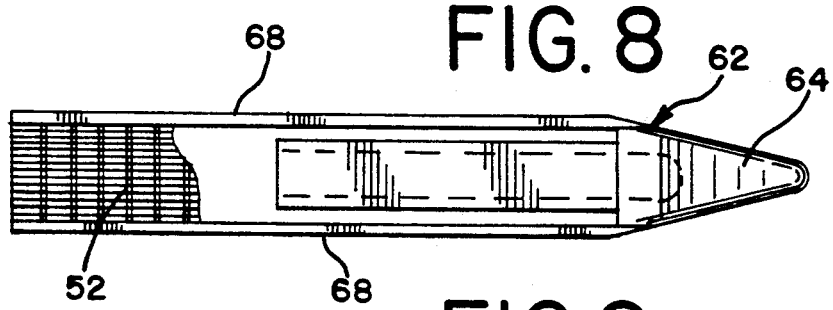
FIG. 8 is a top plan view of the anvil tip shown in FIG. 7.
Figure 9:
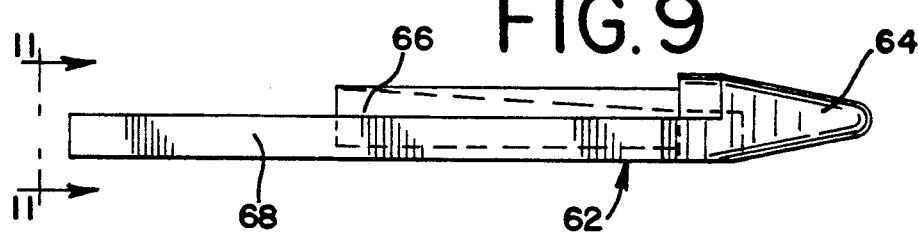
FIG. 9 is a side elevational view of the anvil tip shown in FIG. 7.
Figure 10:
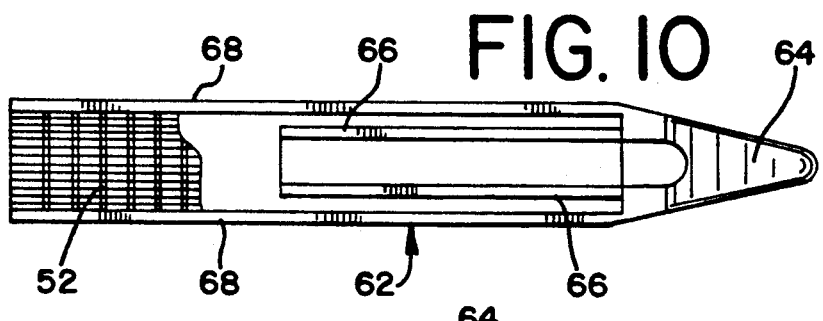
FIG. 10 is a bottom plan view of the anvil tip shown in FIG. 7.
Figure 11:
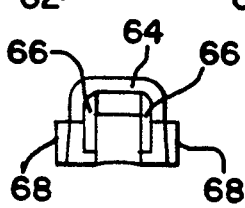
FIG. 11 is an end view of the anvil tip taken along line 11—11 in FIG. 9.

Referring to FIGS. 1 and 3, there is shown a preferred embodiment of a disposable staple cartridge 50 containing a plurality of surgical staples 51, of the type generally disclosed in U.S. Pat. Nos. 4,633,861 and 4,892,244. Cartridge 50 is preferably provided with two pairs of spaced apart parallel lines of staples. Cartridge 50 includes a strip of pledget material 52 releasably attached thereto in covering relationship with the openings 53 through which the staples are ejected. The pledget material strip 52 may be releasably secured to staple cartridge 50 by a variety of means that permit the pledget material strip to remain behind with the staples after the stapler has been removed from the staple site. In accordance with preferred embodiments of the invention, the strip of pledget material is secured to the longitudinal edges of the staple cartridge 50 by a plurality of spaced apart ultrasonic welds or spaced apart adhesive bonds.

Referring to FIGS. 1 and 7-10, the front portion of upper jaw 20 includes an anvil section 60 that includes longitudinal rows of uniformly spaced staple-forming pockets 63. A disposable anvil tip 62 is releasably mounted at the front end of anvil section 60 and is received rearwardly thereinto. Anvil tip 62 includes a leading tapered portion 64 to facilitate the insertion of the jaw member into hollow, tubular body organs or small openings in tissue sections. Anvil tip 62 includes a pair of spaced apart elongated inner side walls 66 that extend into anvil section 60 and a pair of spaced apart elongated outer side walls 68 that extend alongside anvil section 60. A pledget material strip 52 may be releasably secured to anvil tip 62 by a variety of means that permit the pledget material strip to remain behind with the staples after the stapler has been removed from the staple site. In accordance with preferred embodiments of the invention, the strip of pledget material is secured to the bottom surface of the side walls 68 by a plurality of spaced apart ultrasonic welds or spaced apart adhesive bonds.

In accordance with preferred embodiments of the invention, pledget material strips 52 are preferably made from an absorbent material that is absorbable within the body. The material must further have properties that uniformly distribute pressure along the staple line to cause substantial hemostasis along the tissue cut. The pledget material also provides a media for the staples to hold on to in the case of thin or diseased tissue. The material also absorbs impact and reduces trauma. Also, in accordance with a preferred embodiment of the invention the pledget material is a sterile, absorbable, tightly woven fabric prepared by the controlled oxidation of regenerated cellulose fibers. An example of such material is SURGICEL NU-KNIT ® manufactured by Johnson & Johnson of New Brunswick, N.J. Alternative materials may include INSTAT ® and INTERCEED ®, both of which are also manufactured by Johnson & Johnson, and VICRYL FELT ®, manufactured by Ethicon in Germany.

The method for achieving hemostasis along a tissue cut having open blood vessels in accordance with the invention will now be discussed along with a discussion of the operation of stapling device 10. The tissue or walls of organ sections to be stapled and cut are positioned and clamped between upper jaw 20 and lower jaw 40 and latch 38 is in its latched position as shown in FIG. 2. At least one, and preferably both, the cartridge 50 and the anvil tip 62 are provided with a strip of pledget material 52 as discussed above. For example, as shown in FIG. 4, tissue segments 70 and 72 are shown positioned and clamped between jaws 20 and 40.

After the tissue segments are clamped between the jaw members, stapler 10 is fired by advancing firing knob 42 to activate the pusher block and knife blade assembly 30. The firing wedges 32 advance distally through the staple cartridge 50 into engagement with staple drivers to sequentially drive staples 51 through the openings 53 in two pairs of spaced apart parallel lines of staples. The staples 51 contact a corresponding staple forming pocket associated with anvil section 60 to form generally a B-shaped configuration or a flat configuration staple. Referring to FIG. 4, the formed staples extend through the tissue sections 70 and 72 and the strips of pledget material 52. At the same time, knife blade 34 is distally advanced through a longitudinal slot formed in anvil section 60 and staple cartridge 50 to cut the tissue sections gripped between the jaw sections between the two pairs of spaced apart parallel lines of staples.

After the firing wedges 32 are fully advanced to form all of the staples in cartridge 50, the pusher block and knife blade assembly 30 is returned to its start position by retraction of firing knob 42. The latch member 38 may then be moved to its unlatched position, separating jaws 20 and 40, so as to permit the device 10 to be unclamped and removed from the tissue sections releasing the pledget material strips from the anvil tip 62 and/or cartridge 50.

As shown in FIGS. 5 and 6, staples 51 extend through the pledget material strips 52 and the tissue segments 70 and 72 sandwiched therebetween. The pledget material strips 52 uniformly distribute pressure along the line of staples and thereby cause substantial hemostasis along the tissue cut. The pledget material strips also absorb any blood that may escape from a partially open blood vessel. The absorbable nature of the material from which the pledget strips are made allows the strips to be left in the body and eliminates further tissue handling that would be otherwise necessitated by removal of the strips.

In accordance with the most preferred embodiment of the invention the pledget material is positioned adjacent the surfaces of the tissue sections that contact both the staple cartridge 50 and the anvil tip 62. However, the invention contemplates that the pledget material may be positioned adjacent only one of such surfaces, preferably the surface adjacent the anvil tip 62. Further, it is preferred that a pair of parallel lines of staples extend through each tissue section adjacent the tissue cut.

Although disclosed above in conjunction with a particular surgical stapler 10 for exemplary purposes, it is contemplated that the principles of the present invention may be similarly utilized in conjunction with other types of surgical staplers and cutters. For example, a circular stapler of the type disclosed in U.S. Pat. No. 5,104,025 may be suitably modified to provide pledget material on the anvil section of the stapler device. A linear stapler of the type disclosed in U.S. Pat. No. 5,137,198, filed on May 16, 1991, may be suitably modified to provide pledget material on the staple cartridge and the anvil. An endoscopic linear cutter of the type disclosed in U.S. patent application Ser. No. 779,436, filed Oct. 18, 1991, now abandoned, may be suitably modified to provide pledget material on the anvil portion and the staple cartridge assembly.

The method and apparatus of the invention in its broadest aspects is not limited to the specific details shown and described, and modifications may be made to the disclosed preferred embodiments of the invention without departing from the principles of the invention.

What is claimed is:

1. Apparatus for anastomosing the adjacent walls of two organ sections, comprising:
    means for clamping the adjacent walls of the organ sections together with a pledget material that is absorbent and entirely absorbable, said pledge material being positioned between said clamping means and the adjacent surface of at least one of the organ section walls;
    stapling means for forming at least one pair of spaced apart parallel lines of surgical staples extending through the walls of the organ sections and the pledget material so as to substantially uniformly distribute pressure along the lines of the staples; and
    blade means for cutting the walls of the organ sections and the pledget material between the lines of surgical staples while said staples are extended through said walls of the organ and said pledget material so as to the close open blood vessels and cause substantial hemostasis along the cut in the walls of the organ sections.

2. The apparatus as defined in claim 1 wherein said pledget material is positioned between the clamping means and the adjacent surfaces of both of the organ section walls.

3. The apparatus as defined in claim 2 wherein the pledget material is a knitted fabric made from regenerated cellulose fibers.

4. The apparatus as defined in claim 2 wherein said stapling means forms two pairs of spaced apart lines of surgical staples extending through the walls of the organ sections and the pledget material.

5. The apparatus as defined in claim 2 wherein said clamping means includes an upper jaw member and a lower jaw member that are movable toward and away from each other.

6. The apparatus as defined in claim 5 wherein said stapling means includes a staple cartridge containing a plurality of surgical staples attached to one of said upper or lower jaw members and an anvil member attached to the other of said upper or lower jaw members.

7. The apparatus as defined in claim 6 wherein a strip of said pledget material is releasably attached to said staple cartridge.

8. The apparatus as defined in claim 6 wherein a strip of said pledget material is releasably attached to said anvil member.

9. A method of achieving hemostasis along a tissue cut having open blood vessels during the resection of tissue sections, comprising:
    positioning a pledget material that is absorbent and entirely absorbable adjacent at least one surface of the tissue; and
    forming at least one line of surgical staples extending through the tissue and the pledget material so as to substantially uniformly distribute pressure along the staple line closing the open blood vessels and thereby causing substantial hemostasis along the tissue cut.

10. The method as defined in claim 9 wherein a pledget material is positioned adjacent both surfaces of the tissue.

11. The method as defined in claim 9 wherein the pledget material is a knitted fabric made from regenerated cellulose fibers.

12. A method of anastomosing the adjacent walls of two organ sections, comprising the steps of:
    clamping the adjacent walls of the organ sections together with a pledget material that is entirely absorbent and absorbable positioned adjacent the surface of at least one of the organ section walls;
    forming at least one pair of spaced apart parallel lines of surgical staples extending through the walls of the organ sections and the pledget material so as to substantially uniformly distribute pressure along the lines of staples; and
    directing a sharp blade between the parallel lines of surgical staples to cut the walls of the organ sections and the pledget material while said staples are extended through said walls of the organ and said pledget material so as to close the open blood vessels and cause substantial hemostasis along the cut in the walls of the organ sections.

13. The method as defined in claim 12 wherein a pledget material is positioned adjacent the surface of both of the organ section walls.

14. The method as defined in claim 13 including the step of forming two pairs of spaced apart lines of surgical staples extending through the walls of the organ sections and the pledget material.

15. The method as defined in claim 12 wherein the pledget material is a knitted fabric made from regenerated cellulose fibers.

* * * * *